United States Patent [19]

Armeniades et al.

[11] Patent Number: 4,841,984

[45] Date of Patent: Jun. 27, 1989

[54] FLUID-CARRYING COMPONENTS OF APPARATUS FOR AUTOMATIC CONTROL OF INTRAOCULAR PRESSURE

[75] Inventors: C. D. Armeniades; Louise C. Moorhead, both of Houston, Tex.

[73] Assignee: Armoor Ophthalmics, Inc., Houston, Tex.

[21] Appl. No.: 109,077

[22] Filed: Oct. 16, 1987

Related U.S. Application Data

[63] Continuation-in-part of Ser. No. 775,257, Sep. 16, 1985, Pat. No. 4,722,350, which is a continuation-in-part of Ser. No. 653,723, Sep. 21, 1984, abandoned, which is a continuation-in-part of Ser. No. 436,953, Oct. 27, 1982, Pat. No. 4,548,205.

[51] Int. Cl.$^4$ .............................................. A61B 5/00
[52] U.S. Cl. ................................................... 128/748
[58] Field of Search ............... 128/645, 673, 675, 676, 128/748 E; 604/66; 73/721, 66, 727

[56] References Cited

U.S. PATENT DOCUMENTS

| | | | |
|---|---|---|---|
| 3,553,625 | 1/1971 | Chiku et al. | 128/748 X |
| 3,939,823 | 2/1976 | Kaye et al. | 128/748 |
| 4,274,423 | 6/1981 | Mizuno et al. | 128/675 |
| 4,423,727 | 1/1984 | Widron et al. | 128/748 X |

Primary Examiner—Max Hindenburg
Assistant Examiner—John P. Lacyk

[57] ABSTRACT

An ophthalic device and system for measuring and controlling relative fluid pressure inside an ocular globe includes a surgical instrument which is adapted to penetrate the ocular globe. A fluid pressure transducer is mounted on the instrument so that when the instrument penetrates the ocular globe the transducer is located adjacent to an opening that communicates with the interior of the globe so that it can react to pressure changes in the fluid therein and generate signals in response to changes in the pressure of the fluid. The signal is transmitted external of the instrument to a control system which is operatively connected to the transducer for first receiving signals from the transducer and the controlling a fluid supply system in response to signals according to a predetermned set of instructions. The control system is connected to a closed loop feed system in which fluid is continuously circulated. Fluctuations in intraocular pressure cause the control system to divert fluid from the feed system to the ocular globe to a conduit connected to the closed loop.

18 Claims, 7 Drawing Sheets

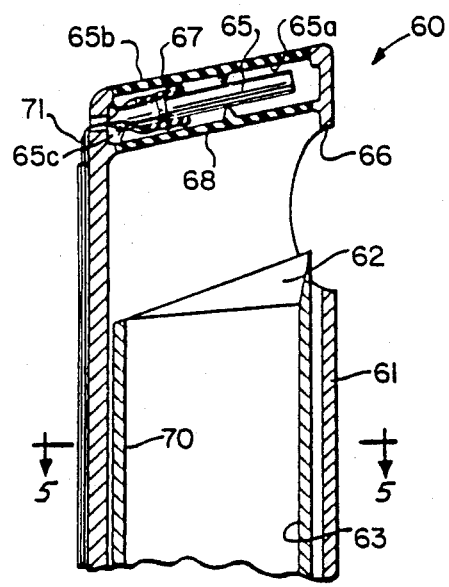
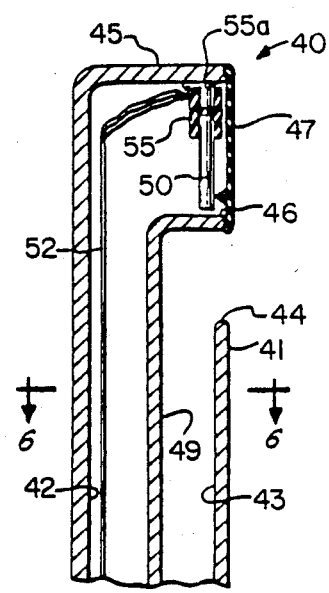
FIG.3
FIG.4
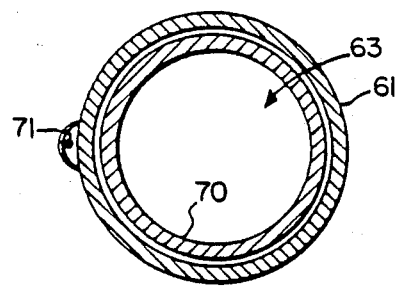
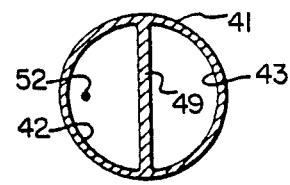
FIG.5
FIG.6

FLUID-CARRYING COMPONENTS OF APPARATUS FOR AUTOMATIC CONTROL OF INTRAOCULAR PRESSURE

CROSS REFERENCES TO RELATED APPLICATIONS

This is a continuation-in-part of pending U.S. application, Ser. No. 775,257, filed Sept. 16, 1985, now U.S. Pat. No. 4,722,350, which was a continuation-in-part of U.S. application, Ser. No. 653,723, filed Sept. 21, 1984, abandoned which was a continuation-in-part of U.S. application Ser. No. 436,953, filed Oct. 17, 1982 now U.S. Pat. No. 4,548,205 issued Oct. 22, 1985.

BACKGROUND OF THE INVENTION

1. Field of Invention

The present invention relates to ophthalmic microsurgical instruments and, more particularly, to such surgical instrumentation which automatically controls internal ocular globe fluid pressure during ophthalmic surgical procedures and the like.

2. General Background

A large number of microsurgical procedures inside the eye are performed through "closed systems" which maintain the integrity and internal pressure of the ocular globe while microsurgical instruments are used to penetrate the eye through one or more small incisions (See FIG. 1). Exemplary functions performed by these instruments are:

fragmentation-the cutting and separation of ocular tissue, such as the lens in cataract surgery or fibrous and membrane-like growths inside the vitreous (e.g., vitrectomy, membraneoctomy);

emulsification-the mechanical digestion of tissue (usually the lens) by means of ultrasound in order to facilitate its removal through small incisions;

irrigation (infusion)-the introduction of a saline solution into the operating field by means of gravity or positive pressure; and aspiration (suction)-the removal of fluid and/or entrained tissue fragments by means of vacuum.

The surgeon combines irrigation and aspiration to transport tissue fragments away from the operating field. He or she also uses these functions to maintain intraocular pressure during the surgical procedure. Control of pressure in irrigation and aspiration is extremely important. If aspiration suction is too strong (due to excessive vacuum), it may damage endothelial cells during anterior chamber surgery or may result in retinal detachment in vitrectomy procedures. Too high an irrigation pressure or excessive variations in the pressuree or flow rate of the irrigation fluid may traumatize ocular tissue.

Instruments for ophthalmic microsurgery made in accordance with prior art are based on the premise that the important parameters in the different surgical procedures are the static levels of intraocular pressure and aspiration vacuum. Static intraocular pressure is controlled by the height (hydrostatic head) of the infusion bottle that contains the saline solution used in ophthalmic surgery. Prior-art instruments provide for raising and lowering of the bottle at the surgeon's command using either manual or mechanical means. Likewise, aspiration vacuum can be controlled by the surgeon by either presetting or continuously varying (via foot-pedal control) the pumping rate in the aspiration line (see for example Douvas: U.S. Pat. No. 4,168,707). In systems where measurement of intraocular pressure is attempted, a pressure sensor is typically placed (at some distance from the ocular globe as taught by Bittner U.S. Pat. No. 3,572,319) and manifested by current commercial instruments.

In February 1986 the inventors of the subject invention published the results of original research (Archives of Ophthalmology, Vol. 104, pp. 269-272) in which they demonstrated on the basis of theory as well as experimental data that the standard surgical maneuvers involved in common ophthalmic procedures (cataract surgery, vitrectomy) produce sudden, large changes in intraocular pressure. These pressure changes are due to perturbations in the rate of fluid flow into or out of the eye associated with enlargement or closing of incisions; the removal of tissue and vitreous humor; and the cutting action of surgical instruments inside the eye. Such sudden pressure changes include "spikes" with peak intensities as high as 160 mm Hg and rapid periodic fluctuations with frequencies as high as 300 cycles per minute. These dynamic changes in intraocular pressure cannot be controlled by manipulation of the infusion bottle height, nor can they be measured at remote locations, such as the console and the fluid line (where the pressure sensors are located in current, commercial instruments) due to rapid attenuation of the pressure disturbances, as they travel along the fluid conduit.

The research findings prompted the subject invention by the same inventors of the invention described in U.S. Pat. No. 4,548,205, which teaches the incorporation of pressure sensor/transducers into various types of infusion or mechanical cutting tips for use inside the eye, so as to provide signals for feedback control of irrigation or aspiration during ophthalmic procedures.

SUMMARY OF THE PRESENT INVENTION

The subject invention is directed to improvements in the fluid-carrying components of the apparatus described in U.S. Pat. No. 4,548,205, which enhance the safety of the apparatus and increase the speed of its response to sudden and/or rapid periodic changes in intraocular pressure.

The apparatus of U.S. Pat. No. 4,548,205 operates to sense intraocular pressure exerted on the tip of a microsurgical instrument or local suction forces on the tissue removed through aspiration. An electrical signal generated in response to relative pressure changes is used to automatically regulate aspiration vacuum level or irrigation flow rate within acceptable ranges for providing an extra measure of safety to those surgical procedures.

The surgical instrument includes a needle-like instrument with a pressure transducer mounted so that, when the instrument penetrates the ocular globe, the transducer lies either immediately outside the globe or inside the globe, where it can communicate directly with the fluid therein. The instrument measures the pressure of the ocular fluid surrounding the instrument relative to ambient atmospheric pressure or local suction forces in the instrument opening exerted on diseased tissue as the tissue is aspirated.

The surgical instrument utilizes a miniature pressure sensor located adjacent to a thin, flexible diaphragm. The diaphragm can be constructed from natural rubber or other suitable elastomer and serves as a barrier between the fluid, the pressure of which is to be measured, and some appropriate reference environment. The diaphragm is connected to the transducer and operates to transmit forces to the transducer as a result of pressure differences between these two environments causing the diaphragm to move.

The transducer is a suitable, miniaturized pressure transducer with appropriate sensitivity and stability. An electric signal is generated by the transducer, which is transmitted to an instrument console where it is amplified and displayed. The signal can be used to activate known feed-back control circuits to operate a valve for regulating or limiting suction vacuum or irrigation fluid through the same or another instrument.

One improvement over the teachings of U.S. Pat. No. 4,548,205 includes a closed loop through which a pump can continuously circulate a saline solution compatible with intraocular fluid. The closed loop system is also equipped with a device to selectively divert saline solution from the closed loop to a transfer conduit which is in communication with the ocular globe. When the transducer detects pressure fluctuation in the eye outside a predetermined range, the signals generated by the transducer, which are received by a microprocessor controller, cause the diverter to either increase or decrease the amount of fluid diverted from the closed loop to the transfer conduit in communication with the ocular globe thereby causing fluid to be supplied to or removed from the eye.

Another improvement is the use of a damping device to attenuate rapid changes in intraocular pressure. The damping device can be in the form of a hollow chamber, capable of holding fluid at a positive pressure, connected by a way of a relief tube to the transfer conduit, which is in communication with the ocular globe. Sudden increases in ocular pressure cause fluid to be expelled through the relief tube into the damping chamber. Sudden decreases in ocular pressure cause fluid to be drawn from the damping chamber through the relief tube, into the eye. When the damping device is used in conjunction with the pressure feedback control system, both devices are capable of reacting to changes in pressure in the frequency range of 0.5 to 10 cycles per second.

Accordingly, it is an object of this invention to provide an ophthalmic surgical instrument which accurately and safely measures the pressure exerted by ocular fluids or tissues at the site of microsurgical activity and to maintain intraocular pressure within safe levels.

Another object of the invention is to provide an accurate pressure signal to feedback control circuits which automatically regulate and/or limit suction vacuum or regulate the flow and pressure of the irrigation fluid in response to sensed intraocular pressure.

The instrument which is the subject of the present invention provides a number of controls during anterior chamber or cataract surgery such as, for example:

1. control of anterior chamber depth (space between cornea and iris);
2. better regulation of bleeding by precise tamponade;
3. accurate measurement of intracular pressure through a second site during wound closure;
4. better control of suture tension during wound closure to avoid astigmatism; and
5. better approximation of physiological intraocular pressure after wound closure.

Controls afforded by the invention during vitreous surgery include:

1. measurement and control of aspiration forces applied to the diseased tissue at the instant of excision and limitation of these forces to avoid retinal detachment;
2. regulation of vitreous pressure from a second site in order to control bleeding during surgery; and
3. better approximation of physiological intraocular pressure after wound closure.

BRIEF DESCRIPTION OF THE DRAWINGS

For a better understanding of the nature and objects of the present invention, reference should be had to the following detailed description, taken in conjunction with the accompanying drawings, in which:

FIG. 3 is a sectional view of one embodiment of the invention where a pressure transducer is mounted to provide communication between the interior of the ocular globe and an internal conduit of the instrument of the type shown in FIG. 2;

FIG. 4 is another embodiment of the invention in which the transducer communicates directly with the interior of the ocular globe;

FIG. 5 is a sectional view looking along lines 5—5 of FIG. 3;

FIG. 6 is a sectional view looking along lines 6—6 of FIG. 4;

DETAILED DESCRIPTION OF PREFERRED EMBODIMENTS

Figure 1:
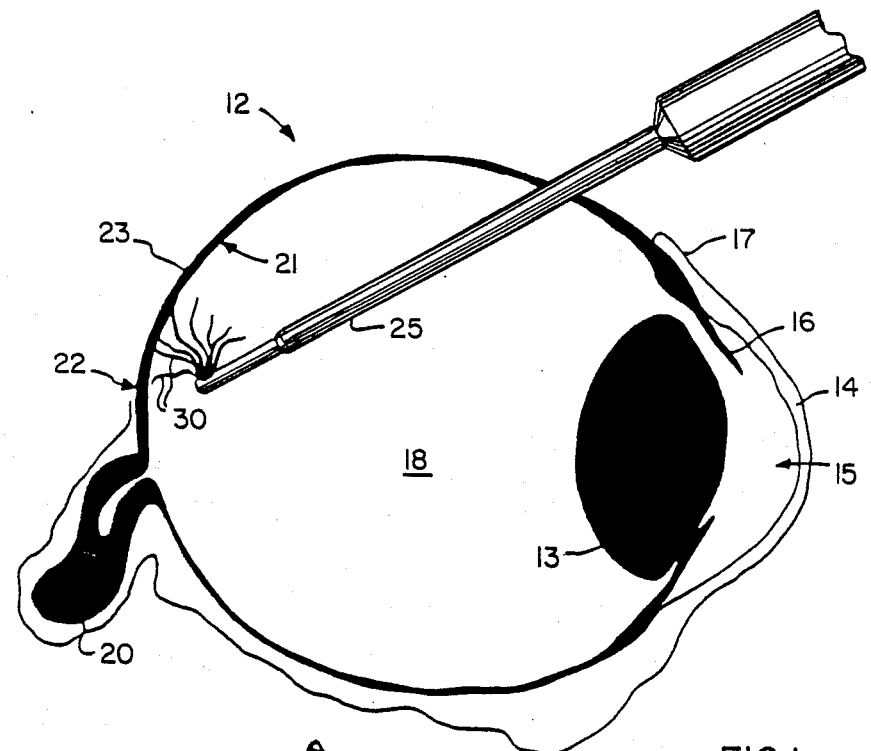
FIG. 1 is a schematic section view illustrating a "closed system" surgical procedure in the eye.
Figure 2:
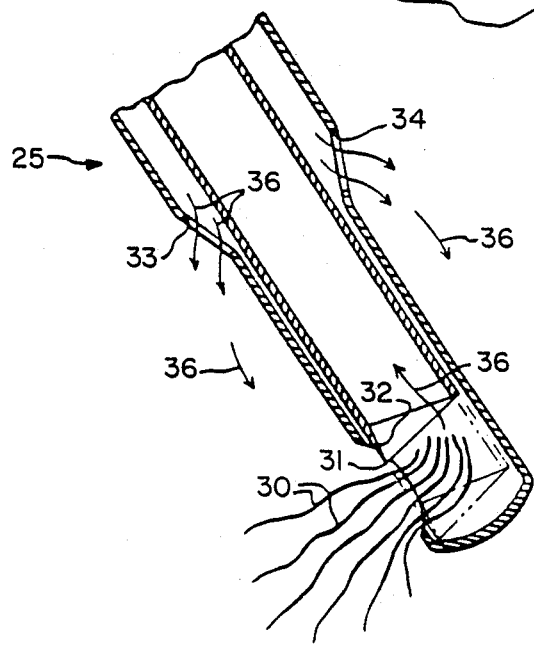
FIG. 2 is a sectional view of the tip of a microsurgical instrument for performing vitreous surgery which is known in the prior art.

FIG. 1 illustrates an ocular globe or eye 12 which includes a lens 13, cornea 14, anterior chamber 15, iris 16, ciliary body 17, vitreous body 18, optic nerve 20, retina 20, cilera 22 and choroid 23. An instrument 25, the tip of which is shown in greater detail in FIG. 2, is a surgical needle 0.4 to 1.00 mm in outside diameter formed of stainless steel which is attached to a handpiece (not shown) for manipulation by the surgeon. The handpiece can be connected through flexible plastic tubing (not shown) to both a saline solution reservoir for irrigation (not shown) and a pumping system for aspiration (not shown). The details of elements not shown are known to those with ordinary skill in the art and need not be described in detail in order to practice the invention.

The instrument 25 is known as an irrigation/aspiration/cutting tip and is shown in FIG. 1 as being inserted in the vitreous 18. Section is used to aspiration diseased tissue 30 into a side opening 31 of the instrument 25. As shown best in FIG. 2, the tissue is cut by a curved micro guillotine blade 32 which is actuated by the surgeon and slidable in the instrument 25. A saline solution or the like is discharged through outlets 33, 34, and infuses the operation site. The infusion, in combination with controlled section through the opening 31, helps to draw the tissue fragments 30 into the instrument 25 for removal after they are cut by the blade 32. Arrow 36 in FIG. 2 illustrates both the discharge of the saline solution and suction action mentioned above.

The conventional instrument shown in FIGS. 1 and 2, however, has no provision for accurately measuring the local section force used to draw the diseased tissue 30 into the instrument 25 prior to cutting. Since the tissue removed by the vitrectomy procedures is usually located in the immediate vicinity of the retina 21, the danger of an inadvertent damage of the retina 21 or other healthy tissue by excessive suction force during vitrectomy is considerable.

The embodiment of the invention illustrated in FIGS. 3 and 5 solves this problem by enabling the suction force to be monitored constantly. An instrument similar to the one in FIGS. 1 and 2 has been modified to measure pressure differences between the external and internal forces of its irrigation/aspiration/cutting tip. The modified instrument is referred to generally by reference numeral 60 and includes an outer elongated housing 61 which surrounds an inner concentric guillotine 70 which carries a cutting blade 62 that cooperates with an opening 66 for surgically removing tissue fragments as described above. An inner bore or channel 63 operates to convey fluid and/or tissue. Only the tip of such an instrument is shown in FIG. 3 and additional features such as the discharge outlets 33, 34, shown in FIG. 2 were omitted to simplify the description.

A pressure transducer 65 is mounted in a chamber 65a located near aspiration inlet 66, the chamber 65a being bounded by two parallel diaphragms 67, 68, formed of the silicon rubber inserts that are about 1 mm in diameter. The diaphragms 67, 68, are connected to the instrument 60 by means of an epoxy resin. The transducer 65 is preferably mounted at the outer end 61a of the tip of the housing 61.

Pressure transducer 65 is a piezo-electric or photoelectric device known to the art which is capable of measuring intraocular pressure with the required sensitivity (plus or minus 1 mm Hg), stability and linearity. Other types of transducers, such as sensors operating in conjunction with fiber-optic light guides which transmit signals in the form of variations in light intensity caused by pressure differences moving a reflective surface, can also be used in conjunction with the invention without substantially altering the size, shape or function of the instrument. An electrical signal generated by the transducer 65 is carried through wire leads 61 to a monitor console which is known in the art and contains a suitable power supply as well as the necessary electrical circuits for conditioning, amplifying the displaying the pressure measurement.

The piezo-electric elements 65b are attached to a cantilever beam and a rigid base 65c, which is anchored to the wall of the instrument. Wire leads 71, which carry electrical signals from the transducer 65, are connected to the exterior surface of the instrument 60 so as to avoid interference with the action of the guillotine cutter 70. The leads 71 are bonded to the instrument 60 so that they are part of its smooth outer surface.

The vitrectomy suction instrument 60 significantly enhances safety through sensitivity to suction force and consequently intraocular pressure during surgery. As the surgeon aspirates strands of diseased tissue into the opening 66, the local pressure difference measured between diaphragms 67, 68, by the transducer 65 results in a relative pressure reading that reflects the forces exerted on the tissue strands as they enter the aspiration inlet 66. These forces fluctuation continuously because of differences in the viscoelastic properties of the manipulated tissue and the viscosity of the surrounding vitreous. The force level at any given time can fall in a range that departs considerably from the average force and the pressure in the vacuum line can be adjusted to accommodate these fluctuating force levels. By using the transducer 65, a signal can be generated to activate momentarily a vacuum relief valve in a known way (not shown) when the local pressure exceeds preset levels to adjust the suction when the force level falls outside the permissible range. Thus, the instrument 60 operates to reduce considerably the danger of damage to healthy tissue by preventing excessive instantaneous peaks in the local suction forces.

Referring to FIGS. 4 and 6, another embodiment of the invention is illustrated, this one being directed to a surgical instrument which can measure intraocular pressures while performing an irrigation or aspiration procedure. The instrument is generally designated by reference numeral 40 and is an elongated body 41 formed of surgical grade stainless steel which an outside diameter of approximately 1 mm. The body 41 is divided through substantially its entire length into two parallel channels 42, 43, that are separated by a internal wall 49. Channel 43 is an irrigation/aspiration channel which is connected to a handpiece (not shown) to either a vacuum system (not shown) or a saline supply reservoir. The channel 43 has an outlet 44 located near the apex 45 of the tip of the instrument 40.

A transducer 50 is mounted in the portion of the channel 42 adjacent to the tip of the instrument 40, the channel 42 being vented to the atmosphere at a suitable site away from the operating field. The transducer 50 is of the type described above where the embodiment of FIGS. 3 and 5 and is connected to the instrument 40 through a base 55a. At the tip of the instrument 40, the transducer 42 terminates at a window 46 which is located adjacent to the outlet 44. The window 46 is approximately 1 mm in diameter and is fitted with a diaphragm 47 formed of silicon rubber. The diaphragm 47 is connected to a window 46 by means of epoxy resin. Wire leads designated by reference numeral 52 carry electrical signals generated by the transducer 50 to suitable instrumentation (such as that described below) for translating the signals into useful information for monitoring and regulating intraocular pressure.

The intraocular pressure probe 40 is suitable for measurement and control of intraocular pressure during closed system procedures in the anterior chamber 15 as well as in the vitreous chamber 18. The instrument 40 can be inserted at a site separate from the operating incision and remain in place throughout the entire procedure, providing the surgeon an independent source of determining and/or controlling intraocular pressure for providing information used in tamponade, suture tension controls and final approximation of physiological pressure at the end of wound closure.

One disadvantage of placing the transducer in the portion of the probe that penetrates the eye, as done in instruments 40 and 60 (see FIGS. 4 and 3, respectively), is that this configuration requires the probe to have a larger diameter than would be otherwise necessary. This problem can be eliminated without affecting the accuracy or speed of the device by relocating the pressure sensitive diaphragm and the transducer outside the eye but in a position where significant signal can be generated in response to changes in intraocular pressure.

Figure 7:
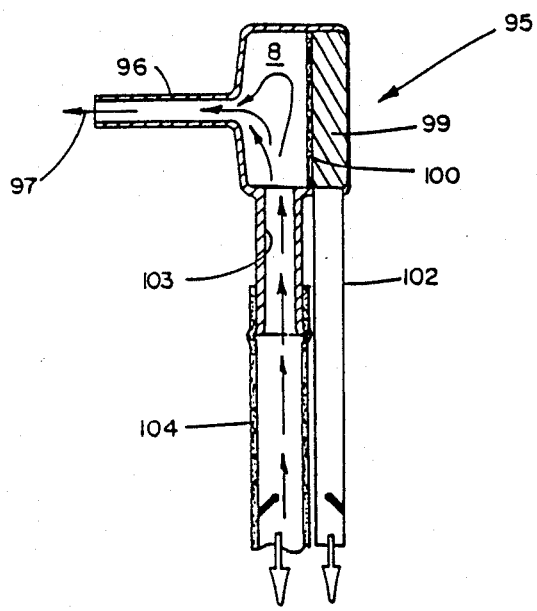
FIG. 7 is a sectional view of another embodiment of the instrument similar to those of FIGS. 3–6, in which the transducer is located outside the eye but adjacent to an opening that communicates with the interior of the eye when the instrument penetrates it.

FIG. 7 illustrates one such alternative embodiment of the invention. The instrument, generally designated by reference numeral 95, includes an elongated needle section 96 with an opening 97 which can be inserted into the ocular globe. The opposite end of the needle section 96 opens into a chamber 98 which is designed to remain outside the ocular globe. A transducr 99 is mounted in the chamber 98 opposite the opening 97. Although the transducer 99 is not located inside the ocular globe, it position adjacent to the opening into the globe supplies a pressure reading nearly as accurate as one obtained through internal placement.

The transducer 99 can be of the type described above for the embodiments illustrated in FIGS. 3–6, or refused silicon-type such as Antran Model No. EPIL-F080-55 manufactured by Antran Devices, Inc., Fairfield, NJ, which is separated from the chamber 98 by a diaphragm 100 formed of paraline, or the like. Wire leads 102 carry electrical signals generated by the transducer 99 to external instrumentation that is described in detail below. The chamber 98 is equipped with an input opening 103 that can be connected to a flexible plastic tubing 104 for supplying fluid in appropriate amounts to the ocular globe.

The instruments shown in FIGS. 3–5 and 7 can be incorporated into any number of systems for controlling pressure within the ocular globe 12. For example, signals generated by the transducer can be used to control the suction level through the same probe on which the transducer is located (FIGS. 1 and 2) or a second probe when the surgical procedure requires fluid to be circulated through the eye. For other surgical procedures, pressure in the eye can be maintained within the predetermined range through a single probe.

Figure 8:
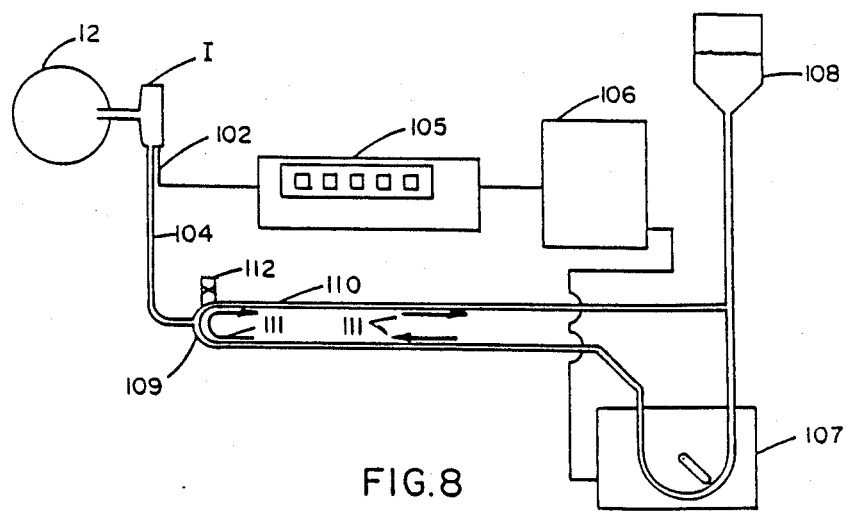
FIG. 8 represents a schematic view of an embodiment of a closed loop system where the pressure transducer is mounted on a surgical instrument responsible for irrigation/aspiration as shown in FIGS. 3–7.
Figure 9:
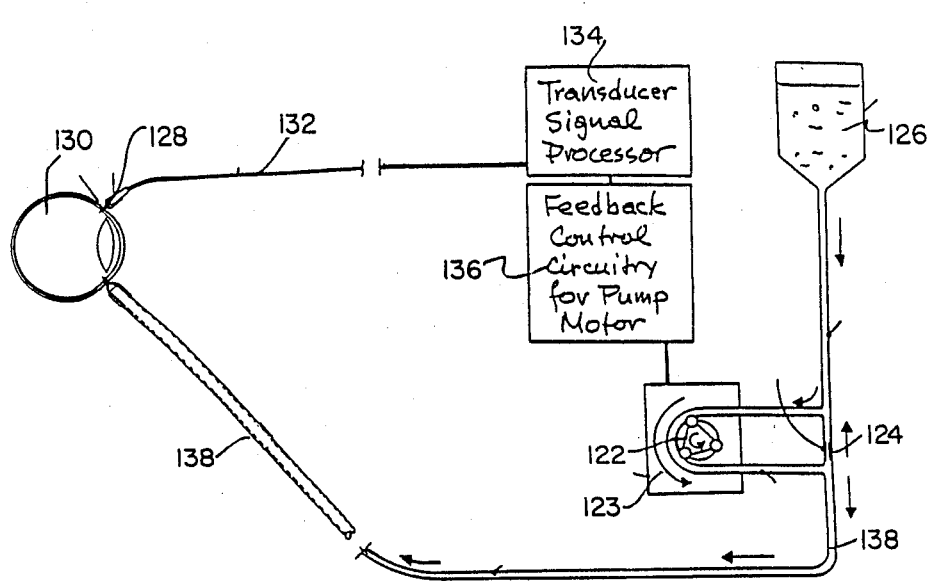
FIGS. 9, 9A and 9B represent a second embodiment of a closed loop system where a flow restrictor is used.
Figure 10:
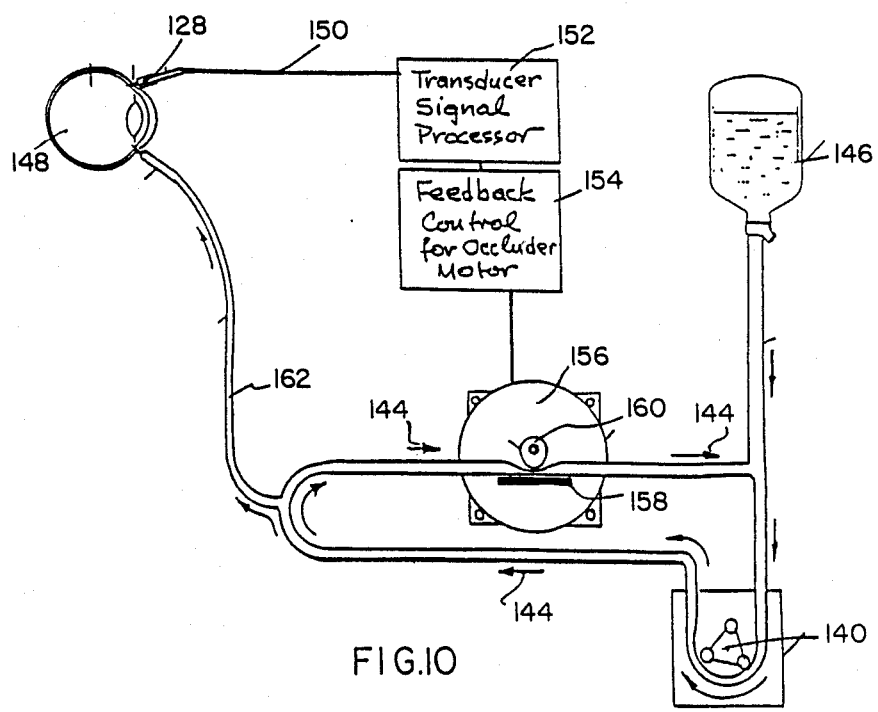
FIG. 10 represents a third embodiment of a closed loop system.

The instruments described above can be used in a system of the type shown in FIGS. 8, 9 or 10 where a pressure level within a predetermined range is maintained and controlled more accurately than in any other known system. This is accomplished through the use of a closed feed loop through which saline solution is continuously circulated. This closed circuit feed loop is connected to a conduit that is in turn connected to the eye so that reaction to a change in pressure detected by the transducer, will act to supply or withdraw fluid from the eye as required, thereby controlling intraocular pressure.

Referring to FIG. 8, an instrument I of the type shown in FIGS. 3–6 or 7 penetrates the ocular globe 12 and is connected to a fluid conduit 104. A flow loop 110 is connected to the conduit 104 through a flow splitter connection 109. When the system is operating, a peristaltic pump 107 continuously circulates saline solution through the loop 110 in the direction of arrows 111. A reservoir of saline solution 108 is connected to the loop 110 for supplying additional solution when needed. A pressure relief value 112 can be provided at the splitter connection 109, but it is not considered necessary for successful operation of the circuit.

If the instrument 100 detects a pressure change in the ocular globe 12, a signal is transmitted through a line 102 to a monitor/console 105 of a type known in the art, which contains a suitable power supply as well as the necessary electrical circuits for conditioning, amplifying and displaying the pressure measurements. The signal is in turn transmitted to a microprocessor controller 106 of a type known in the art, which is operatively connected to the pump 107.

The microprocessor controller is programmed to allow the pump 107 to circulate fluid though the loop 110 at a predetermined flow rate when signals received from the transducer indicate that the pressure of intraocular fluid is within a preset range. This flow rate will operate to maintain a predetermined pressure when a pressure drop is detected by the instrument I; the resulting signal to the microprocessor controller operates to speed up the pump a predetermined amount for infusing additional saline solution into the eye.

Conversely, if a pressure increase is detected, the pump speed is reduced. The use of a flow splitter in relatively close proximity to the instrument 100 (for example, by resting it on the forehead of the patient) and the continuously circulating saline solution in the loop 110 provide for a much more rapid response to pressure changes in the eye than if a long fluid column were used or if a pump had to be activated in response to each pressure change.

FIG. 9 illustrates an alternative embodiment of the closed-loop circuit. A saline solution is continuously circulated in the feed conduit loop 120 by a variable speed peristaltic pump 122 in the direction of arrow 123. A fixed flow restrictor 124 is located within the conduit loop 120. A suitable reservoir 126, in which saline solution is stored, supplies additional saline solution to the conduit loop 120 as needed.

When an instrument 128 of the type shown in FIGS. 3–6 or 7 detects a pressure change in the ocular globe 130, a signal is transmitted through a line 132 to a monitor/console 134 of a type known in the art, which contains a suitable power supply as well as the necessary electrical circuits for conditioning, amplifying and displaying the pressure measurements. The signal is in turn transmitted to a microprocessor controller 136 of a type known in the art, which is operatively connected to the pump 122.

The microprocessor controller is programmed to allow the pump 122 to circulate fluid though the conduit loop 120 at a predetermined flow rate when signals received from the transducer indicate that the pressure of the intraocular fluid is within a preset range. This flow rate operates to maintan a predetermined pressure level within the ocular globe 130. However, if a pressure drop is detected by the instrument 120, the resulting pressure signal to the microprocessor controller operates to speed up the pump 122 and raise the pressure of the circulating saline solution. The fixed flow restrictor 124 in turn causes an increased amount of the circulating saline solution to be diverted into the conduit 138, resulting in additional saline solution to be infused into the eye 130. Conversely, if an increase in intraocular pressure is detected, the pump speed is reduced which operates to decrease the back pressure and reduce flow through the restrictor 124. Less fluid is diverted into the conduit 138, which reduces pressure in the conduit 138 and allows a net outflow of fluid from the eye 130.

Figure 9A:
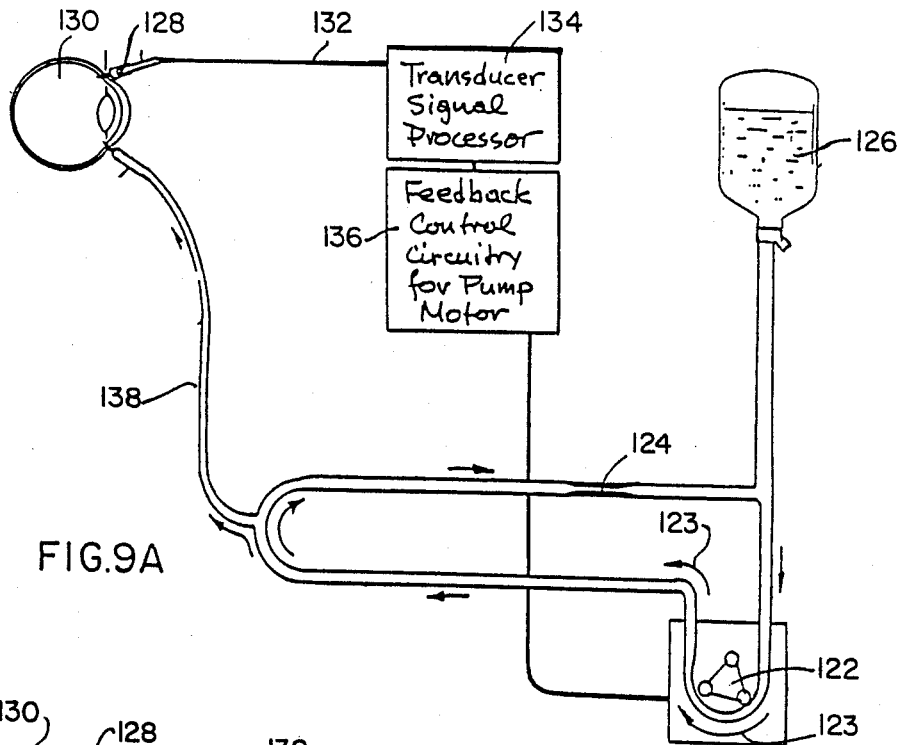
Figure 9B:
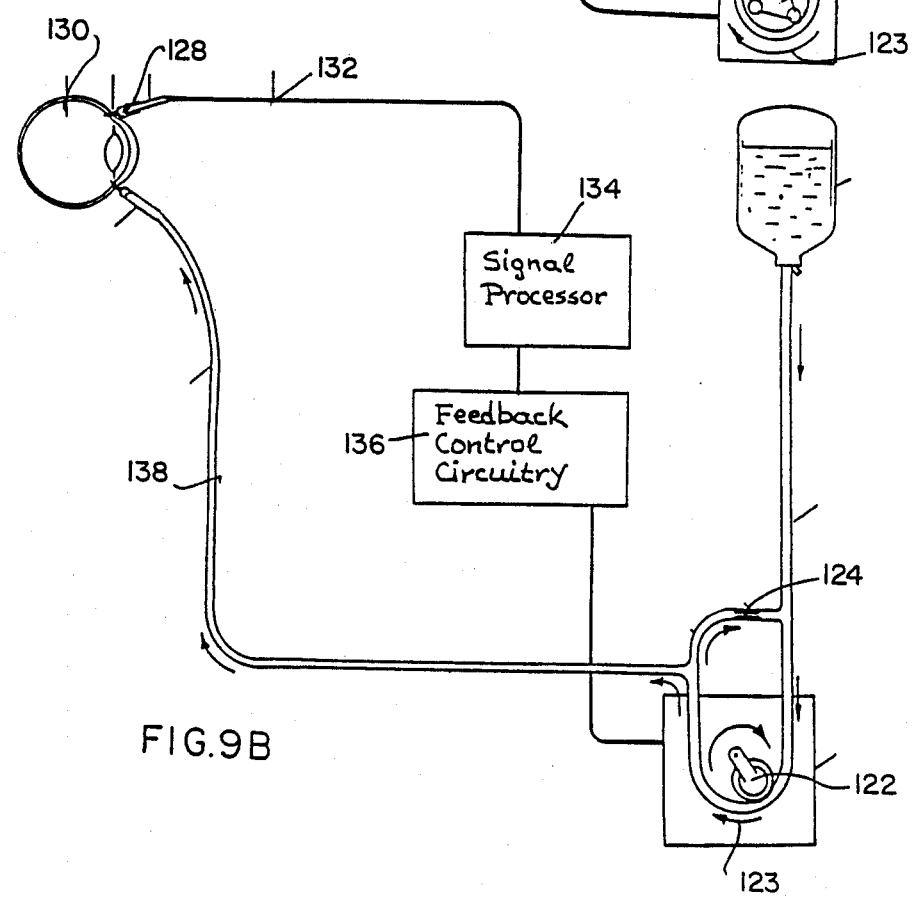

FIGS. 9A and 9B show the use of a fixed flow restrictor at other locations in the conduit loop 120. In both FIGS. the restrictor is located between the conduit 138 and reservoir 126, with the FIGS. showing different configurations of the conduit loop 120.

Another embodiment of the invention is shown in FIG. 10, where an instrument 128 of the type shown in FIGS. 3-6 or 7 is in turn connected to an ocular globe 130. When the system is operating, a peristaltic pump 140 continuously circulates saline solution through a feed conduit loop 142 in the direction of the arrows 144. A suitable reservoir 146 containing saline solution is connected to the loop 140 for supplying additional solution when needed.

When the instrument 128 detects a pressure change in the eye 148, a signal is transmitted through a line 150 to a monitor/console 152, similar to the monitor/console 134 described above in conjunction with FIG. 9. The signal is in turn transmitted to a microprocessor controller 154 of a type known in the art, which is operatively connected to a stepper motor 156 mounted on a base 158. The conduit loop 140 is formed of a flexible tubing so that a rotating eccentric cam 160 mounted on the stepper motor 156 can controll the flow of saline solution through the tubing by alternately pinching and releasing a pinching force on the line depending on the position of the cam 160.

The micoprocessor controller 154 is programmed to allow the pump 142 to circulate fluid through the loop 140 at a predetermined flow rate when signals received from the transducer in the instrument 128 indicate that the pressure of the intraocular fluid is within a preset range. This flow rate operates to maintain a predetermined pressure level within the ocular globe 148. If a pressure drop is detected, the resulting signal operates to activate the stepper motor 156, which rotates the cam to pinch the flexible feed conduit tubing against the base 158, creating a back flow pressure which diverts additional fluid to conduit 162 and infuses additional saline solution into the eye 148. Conversely, if a pressure increase is detected, the stepper motor 156 rotates the cam 160 to a position that enlarges the opening in the flexible, tubing permitting flow to increase within the feed circuit loop 140 and consequently lower the intraocular pressure.

Incorporation of a closed loop in the infusion fluid conduit, as exemplified by the embodiments of FIGS. 8-10, increases significantly the response speed of the fluid delivery system to changes in intraocular pressure, as compared to a simple infusion conduit from the pump to the eye. In addition, conduit loops of the types described provide an important safety element in the event of pump stoppage, due to equipment malfunction. The system can revert to passive, gravity flow from the infusion bottle through the return portion of the loop of the eye, thus bypassing a stalled pump or other malfunction.

It has been found that the effectiveness of the pressure-activated, feedback-controlled system in responding to rapid fluctuations in intraocular pressure reaches an upper limit at fluctuation frequencies of ca. 200 per minute. Pressure changes in this frequency range can be effectively attenuated by the use of damping devices, described in greater detail below, which are mounted in series or parallel with the fluid infusion conduit in close proximity to the infusion cannula. In general, these damping devices utilize the elasticity of thin membranes or the damping properties of air or other gases, confined into a small chamber.

Figure 11:
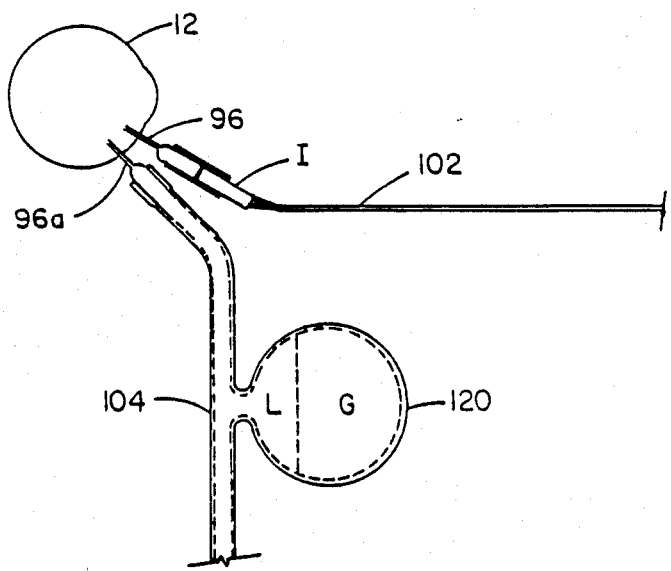
FIG. 11 is a schematic view of a damping chamber that can be incorporated into the systems of FIGS. 8, 9 or 10.
Figure 12:
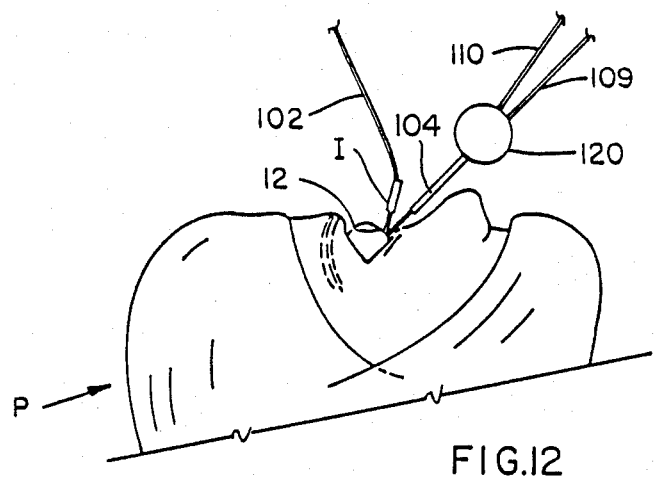
FIG. 12 is another embodiment of a damping chamber shown in use on a patient.

One embodiment of such a damping chamber is shown in FIGS. 11 and 12, where a damping or compliance chamber 120 is connected to a fluid conduit 104, either downstream from a splitter connection (FIG. 11) or at the splitter connection 109 (FIG. 12). The compliance chamber 120 operates to accommodate sudden changes in pressure in the ocular globe 12 caused by surgical manipulations such as pressing on the globe, pulling on the ocular muscles or tightening of stitches where pressure is raised or starting or enlarging an incision where pressure is lowered. Such pressure fluctuations tend to be very rapid, on the order of $10^{-2}$–$10^{-1}$ per second. The normal response time of the systems, shown in FIGS. 8–10 might not be fast enough to react to many such pressure fluctuations because of inertial and frictional forces in the equipment and associated flow lines.

In order to provide a quicker response time to these sudden fluctuations, the compliance chamber 120 is included in the flow line leading to the eye, in close proximity to eye. Preferably, the compliance chamber 120 is located from 6–10 cm. from the tip of needle section 96a.

The compliance chamber 120 in FIG. 11 is formed as a small, spherical chamber that is 4–8 cm. in diameter with highly elastic walls. The compliance chamber 120 can be completely filled with the fluid F flowing through the flow lines 102, 104 (FIG. 12). However, the reaction time to intraocular pressure changes can be increased by initially filling the chamber 120 with air or other gas G, as shown in FIG. 11, for more rapidly accommodating pressure changes because of the greater compressibility of the gas G.

As shown in FIG. 11, the compliance chamber 120 can be formed as part of or connected to the conduit 104, downstream from the splitter connection 109. In such case, the conduit 104 can be formed separately from the conduit 102, with individual needle sections 96, 96a, respectively, connected to the flow line 104 and instrument I as described above. Alternatively, as shown in FIG. 11, the compliance chamber 120 can be connected to the loop 110 at the flow splitter connection 109.

Figure 13:
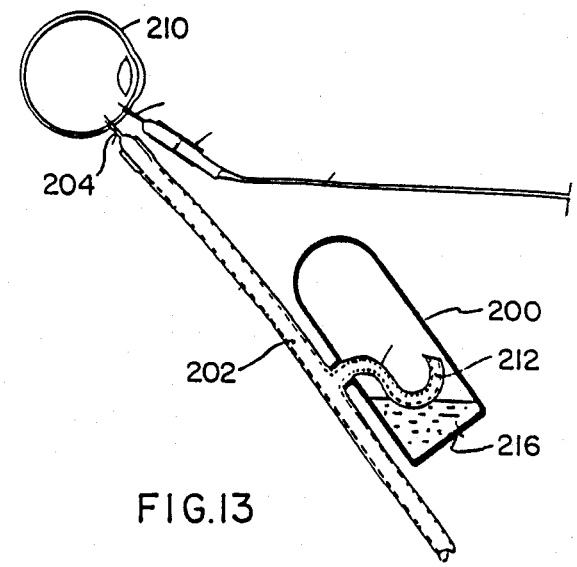
FIG. 13 is a sectional view of a third embodiment of a damping chamber.
Figure 14:
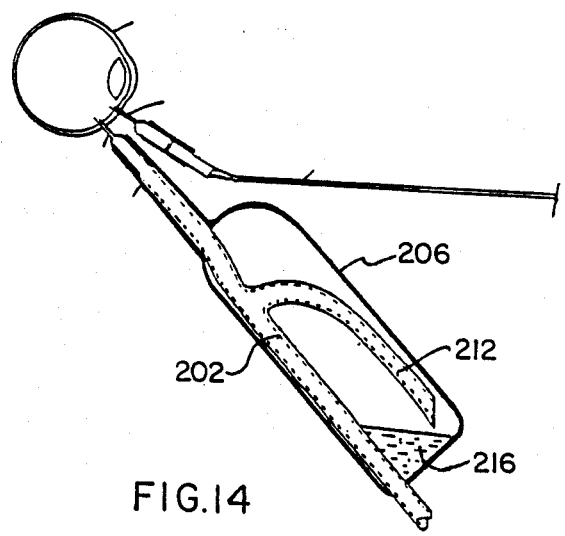
FIGS. 14 and 14A are sectional views of other embodiments of a damping chamber.
Figure 14A:
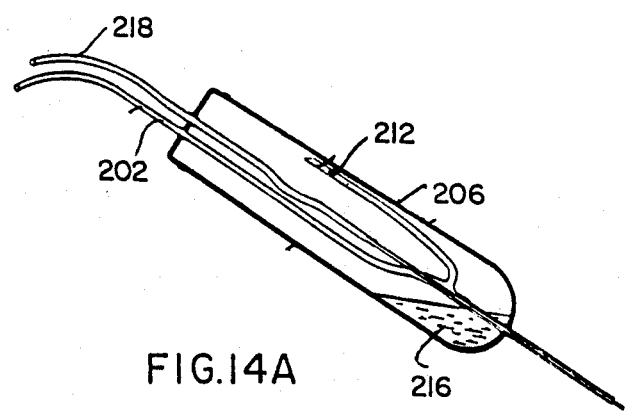

FIGS. 13, 14 and 14a show additional embodiments of these damping devices in the form of small thin walled air chambers, a few cubic centimeters in volume, constructed from metal, rigid plastic, or other sitable material. In FIG. 13 the damping chamber 200 is attached to an infusion conduit 202, close to the inflow cannula 204. FIG. 14 shows a damping chamber built into the hollow handle of an irrigation handpiece 206.

Sudden increases in intraocular pressure cause a small amount of fluid to be expelled from the ocular globe 210 and backflow into an open tube 212 inside the damping chamber, thus relieving pressure in the eye and compressing the air in the damping chamber. The opposite happens with sudden reductions in intraocular pressure, which cause the fluid in tube 212 to flow forward into the eye 210. In FIG. 14A, aside from the different configuration of the tube 212, an aspiration line 218 leading to a vacuum pump (not shown) is shown in the handpiece 206.

The damping characteristics of these air chambers may be fine-tuned to the size and elasticity of the particular ocular globe involved in a given procedure by varying the air-chamber volume. This can be done by the surgeon at the start of the procedure, by holding the chamber 200 or 205 upside-down, thus allowing a variable amount of irrigation fluid 216 to enter the chamber and remain there during the procedure. Similar tuning takes place automatically during the procedure in the event of deliberate increase in the pressure setting, e.g., when the surgeon uses tamponade to stop bleeding; the increase in infusion line pressure forces infusion fluid into the air chamber, thus decreasing its volume until equilibrium is reestablished at the high pressure level.

These damping devices are optimally used in conjunction with a feedback-controlled infusion system of the type described above in conjunction with FIGS. 8-10, whereby the two systems act in concert. However, the damping devices may be used alone, if desired, thereby providing only attenuation of transient and rapid periodic pressure changes, without overall pressure control.

The automatic maintenance and control of intraocular pressure, achieved by the foregoing invention has significant therapeutic potential in reducing edema in the retina after vitrectomy, decreasing intraocular inflammation after irrigation/aspiration procedures and minimizing postoperative astigmatism incurred during wound closure in cataract surgery.

The inventions embodied in the instruments and apparatus above are useful in constantaly monitoring and controlling both intraocular fluid pressure and suction forces during ophthalmic surgery. By allow the surgeon the benefit of this type of equipment, much of the guesswork of maintaining optimum intraocular pressure during surgery is removed, resulting in safer, more accurate surgical procedures. Moreover, the control systems can automatically regulate intraocular pressure according to a predetermined set of instructions more rapidly and accurately than before.

Although different embodiments of the invention may vary in detail. They are still intended to be within the scope of the inventive concept described above. The details described in the foregoing preferred embodiments are intended to illustrative and not limiting in any sense.

I claim:

1. An apparatus for controlling fluid pressure in an ocular globe, comprising:
   (a) a transfer conduit means adapted to communicate with the interior of the ocular globe; and
   (b) damping means communicating with the transfer conduit means for attenuating transient and rapid periodic disturbances in intraocular pressure.

2. The apparatus of claim 1 further comprising:
   a fluid reservoir communicating with the transfer conduit for supplying fluid to the ocular globe; and
   means for supplying fluid through the transfer conduit means to the ocular globe.

3. The apparatus of claim 1, wherein the damping means include a damping chamber and a relief tube with one end in the damping chamber and the other end connected to the transfer conduit, said one end being adapted to be positioned above a quantity of fluid in the chamber for attenuating sudden changes in intraocular pressure.

4. The apparatus of claim 3, wherein the damping chamber is a thin-walled air chamber constructed of a rigid material.

5. The apparatus of claim 3, wherein the damping means includes a hollow enclosed handle for holding the transfer conduit means and comprising the damping chamber.

6. The apparatus of claim 5, wherein an aspiration line is also held by the handle.

7. The apparatus of claim 1, wherein the damping means includes a resilient walled chamber.

8. The apparatus of claim 7, wherein the damping means is adapted to include a quantity of fluid in a portion away from where the damping means is connected to the transfer conduit.

9. The apparatus of claim 1, and further including a fluid infusion conduit, said damping means being mounted in parallel to said fluid infusion conduit.

10. The apparatus of claim 2 wherein said means for supplying being a gravity flow while said fluid reservoir is elevated above the ocular globe 11. An apparatus for controlling fluid pressure in an ocular globe, comprising:
    (a) a transfer conduit means adapted to communicate with the interior of the ocular globe;
    (b) a fluid reservoir communicating with the transfer conduit for supplying fluid to the ocular globe;
    (c) pump means for supplying fluid through the transfer conduit means to the ocular globe;
    (d) pressure sensing means adapted to communicate with fluid in the ocular globe for generating signals in response to changes in intraocular pressure;
    (e) control means for receiving signals from the pressure sensing means and vary the amount of fluid transferred through the transfer conduit means in response to flucuations in intraocular pressure; and
    (f) damping means communicating with the transfer conduit means for attenuating transient and rapid periodic disturbances in intraocular pressure.

12. The apparatus of claim 1, wherein the pressure sensing means includes a surgical instrument adapted to penetrate the ocular globe, and a pressure transducer mounted on the instrument in communication with the intraocular fluid.

13. The apparatus of claim 1, wherein the damping means includes a damping chamber and a relief tube with one end in the damping chamber and the other end connected to the transfer conduit, said one end being adapted to be positioned above a quantity of fluid in the chamber for attenuating sudden changes in intraocular pressure.

14. The apparatus of claim 13, wherein the damping chamber is a thin-walled air chamber constructed a rigid material.

15. The apparatus of claim 13, wherein the damping means includes a hollow enclosed handle for holding the transfer conduit means and comprising the damping chamber.

16. The apparatus of claim 15, wherein an aspiration line is also held by the handle.

17. The apparatus of claim 1, wherein the damping means includes a resilient walled chamber.

18. The apparatus of claim 17, wherein the damping means is adapted to include a quantity of gas in a portion away from where the damping means is connected to the transfer conduit.

* * * * *